(12) United States Patent
Breitenlechner et al.

(10) Patent No.: US 10,224,190 B2
(45) Date of Patent: Mar. 5, 2019

(54) METHOD AND APPARATUS FOR CHEMICAL IONIZATION OF A GAS MIXTURE

(71) Applicant: Universität Innsbruck, Innsbruck (AT)

(72) Inventors: Martin Breitenlechner, Wörgl (AT); Armin Hansel, Innsbruck (AT)

(73) Assignee: Universität Innsbruck, Innsbruck (AT)

( * ) Notice: Subject to any disclaimer, the term of this patent is extended or adjusted under 35 U.S.C. 154(b) by 0 days.

(21) Appl. No.: 15/552,872

(22) PCT Filed: Feb. 24, 2016

(86) PCT No.: PCT/EP2016/053833
§ 371 (c)(1),
(2) Date: Aug. 23, 2017

(87) PCT Pub. No.: WO2016/135179
PCT Pub. Date: Sep. 1, 2016

(65) Prior Publication Data
US 2018/0047550 A1    Feb. 15, 2018

(30) Foreign Application Priority Data
Feb. 25, 2015  (EP) ..................... 15156526

(51) Int. Cl.
*H01J 49/10*      (2006.01)
*H01J 49/00*      (2006.01)
(Continued)

(52) U.S. Cl.
CPC ...... *H01J 49/0027* (2013.01); *G01N 30/7206* (2013.01); *H01J 49/06* (2013.01); *H01J 49/145* (2013.01)

(58) Field of Classification Search
CPC ...... H01J 49/0027; H01J 49/06; H01J 49/145; G01N 30/7206
(Continued)

(56) References Cited

U.S. PATENT DOCUMENTS

| 5,572,035 A | 11/1996 | Franzen |
| 5,811,800 A | 9/1998 | Franzen |

(Continued)

FOREIGN PATENT DOCUMENTS

| DE | 19549144 | 7/1996 |
| DE | 19517507 | 8/1996 |

(Continued)

OTHER PUBLICATIONS

Final Office Action received in corresponding U.S. Appl. No. 14/912,413, dated Aug. 30, 2018.
(Continued)

*Primary Examiner* — Nicole Ippolito
(74) *Attorney, Agent, or Firm* — Lewis & Reese, PLLC (57) ABSTRACT

A method and apparatus for chemical ionization of analyte gas particles in a carrier gas by introducing primary ions, characterized in that the primary and product ions are accelerated by a rotating electric field orthogonal to that direction (5) in which the ions are transported towards the exit (3) of the reaction volume (1). This can, for example, reduce unwanted cluster formation without increasing the transport speed of the ions through the reaction chamber, which improves, for example, the product ion yield. The apparatus of the invention achieves this by means of N≥3 rod electrodes (6) to which N AC voltages $U_1(t), \ldots, U_N(t)$ with N different phase positions ascending in one sense of rotation $\varphi_1, \ldots, \varphi_N$ are applied.

14 Claims, 5 Drawing Sheets

(51) Int. Cl.
  *G01N 30/72* (2006.01)
  *H01J 49/06* (2006.01)
  *H01J 49/14* (2006.01)

(58) Field of Classification Search
  USPC .................. 250/281, 282, 288, 423 R, 424
  See application file for complete search history.

(56) References Cited

U.S. PATENT DOCUMENTS

| | | | |
|---|---|---|---|
| 6,107,628 | A | 8/2000 | Smith et al. |
| 6,674,071 | B2 | 1/2004 | Franzen |
| 2001/0020679 | A1 | 9/2001 | Franzen |
| 2003/0136905 | A1 | 7/2003 | Franzen et al. |
| 2005/0178956 | A1 | 8/2005 | Hansel et al. |
| 2005/0258354 | A1 | 11/2005 | Baba et al. |
| 2006/0219933 | A1 | 10/2006 | Wang |
| 2007/0075240 | A1* | 4/2007 | Hieke .............. H01J 49/04 250/282 |
| 2008/0164409 | A1 | 7/2008 | Schultz et al. |
| 2008/0203287 | A1 | 8/2008 | Crawford |
| 2010/0308218 | A1 | 12/2010 | Wang |
| 2012/0031070 | A1* | 2/2012 | Slough .............. F03H 1/0081 60/202 |
| 2012/0153140 | A1 | 6/2012 | Makarov |
| 2012/0305759 | A1 | 12/2012 | Park |
| 2013/0009051 | A1* | 1/2013 | Park .............. H01J 49/063 250/282 |
| 2015/0340218 | A1* | 11/2015 | Papanastasiou .... H01J 49/0404 250/289 |
| 2016/0181080 | A1 | 6/2016 | Williams |
| 2016/0189948 | A1 | 6/2016 | Breitenlechner |

FOREIGN PATENT DOCUMENTS

| | | |
|---|---|---|
| GB | 2324406 | 10/1998 |
| WO | 93/08589 | 4/1993 |
| WO | 2010/141776 | 12/2010 |
| WO | 2012/123730 | 9/2012 |

OTHER PUBLICATIONS

Hansel, A., et al., "Proton Transfer Reaction Mass Spectrometry: On-line Trace Gas Analysis at the ppb Level," International Journal of Mass Spectrometry and Ion Processes, 149/150, 1995, pp. 609-619.

Jordan, A. et al., "An Online Ultra-high Sensitivity Proton-transfer-reaction Mass-spectrometer Combined with Switchable Reagent Ion Capability (PTR+SRI-MS)," International Journal of Mass Spectrometry, 286, 2009, pp. 32-38.

Barber, Shane et al., Increased Sensitivity in Proton Transfer Reaction Mass Spectrometry by Incorporation of a Radio Frequency Ion Funnel, Analytical Chemistry, 84, 2012, pp. 5387-5391.

Julian, Ryan R., et al., Ion Funnels for the Masses: Experiments and Simulations with a Simplified Ion Funnel, American Society for Mass Spectrometry, 16, 2005, pp. 1708-1712.

Adams, N.G., et al., "The Selected Ion Flow Tube (SIFT); A Technique for Studying Ion-Neutral Reactions," International Journal of Mass Spectrometry and Ion Physics, 21, 1976, pp. 349-359.

International Search Report regarding corresponding PCT Application No. PCT/EP2016/053833, dated Jun. 14, 2016.

* cited by examiner

METHOD AND APPARATUS FOR CHEMICAL IONIZATION OF A GAS MIXTURE

FIELD OF THE INVENTION

The present invention relates to a method and an apparatus for chemical ionization [CI] of a gas mixture or sample gas, for example, by means of ion-atom reactions or ion-molecule reactions [IMR], in particular by means of proton transfer reactions [PTR]. The gas mixture comprises at least a main component or a carrier gas (e.g. $O_2$, $N_2$ or a mixture thereof, e.g. air) and one or more reactant gases or analytes (e.g. volatile organic compounds [VOCs]). Ionization takes place in such a manner that by reactions with primary ions (e.g. $H_3O^+$, $NH_3^+$, $NO^+$, $O_2^+$, $NO_3^-$) additionally introduced into the gas mixture, product ions are generated from non-ionized atoms or molecules of the reactant gases. The reactant gases are in most cases present in very small concentrations, typically in the ppbv to pptv range (i.e. parts per billion/trillion by volume).

The invention also relates to the use of the method according to the invention and/or of the apparatus according to the invention in methods and/or apparatuses for analyzing the properties of a gas mixture or sample gas, in particular for an analysis using CI mass spectrometers, in particular IMR and PTR mass spectrometers.

INTRODUCTION

In methods and apparatuses for an (at least partial) chemical ionization of a gas mixture or sample gas, which comprises a main component or carrier gas (e.g. $O_2$, $N_2$ or a mixture thereof, e.g. air) and one or more reactant gases or analytes (e.g. volatile organic compounds [VOCs]) (in most cases present in very small concentrations), chemical ionization [CI] of particles (i.e. atoms or molecules) of the reactant gases takes place in that primary ions are introduced into the sample gas and so-called product ions are generated from the previously neutral reactant gas particles by reactions between the primary ions and the reactant gas particles, wherein these ionizing reactions can also comprise a plurality of reaction steps. The ionization of particles of the carrier gas is in most cases not intended. After the ionization process, the product ions and the remaining primary ions are supplied either immediately to an ion-selective analyzer/detector unit (e.g. a mass spectrometer or an ion mobility spectrometer) or to further method steps.

A specific kind (i.e. a sub-group) of chemical ionization processes are the so-called proton transfer reactions [PTR]. In these processes, a reactant gas particle R is ionized by transferring a proton $H^+$ of a primary ion $XH^+$, so that a product ion $RH^+$ is formed and the primary ion $XH^+$ becomes a neutral molecule X:

A plurality of chemical ionization processes are known, and accordingly there is also a plurality of known primary ions of both polarities which are suitable for the chemical ionization (e.g. $H_3O^+$, $NH_3^+$, $NO^+$, $O_2^+$, $NO_3^-$) and an even larger number of known atoms and molecules which can be ionized by CI processes (e.g. very many volatile organic compounds [VOCs]).

Chemical ionization processes are "gentle" in the meaning that less energy is transferred to the generated product ion than in many other ionization processes (e.g. electron impact ionization). CI processes are therefore particularly advantageous for the ionization of molecules whose product ions fragment easily, i.e. whose product ions break apart already at low excitation energies. Therefore, CI processes are particularly advantageous for applications in which the sample gas to be ionized contains molecules whose product ions fragment easily (e.g. VOCs) but whose fragmentation is undesired.

One of the most important main applications of methods and apparatuses for the chemical ionization of a sample gas is CI mass spectrometry, in particular analytical CI mass spectrometry, i.e. that in connection with the analysis of the sample gas it is not only intended to determine the masses or the types of the analyte gas particles contained in the sample gas but it is also intended to measure the concentrations of the analyte gas particles absolutely or relative to each other quantitatively.

CI mass spectrometry is a meanwhile very highly developed technical field, so that this field provides most of the prior art relating to methods and apparatuses for the ionization of a sample gas by means of chemical ionization [CI]. Of course also other applications of CI processes are known and conceivable, e.g. ion mobility spectroscopy. The use of the present invention in such other applications is also comprised by the invention, even if these further applications will not be dealt with in detail in the following.

The most common types of CI mass spectrometers comprise the following devices or assemblies:

(i) A primary ion source in which the primary ions are generated and, if necessary, selected so that only ions of the desired type are present at the exit of the primary ion source.

(ii) A so-called "reaction chamber" in which the space (in the following called "reaction volume" or "reaction area") is located in which the primary ions interact with the sample gas and thus the product ions are generated. In many cases, this reaction chamber is configured such that the primary and product ions are also transported and/or guided and/or focused therein—in most cases by means of electric fields.

(iii) A mass spectrometer to which the product ions generated in the reaction chamber and in most cases also the remaining primary ions are supplied in order to determine their masses and preferably also their (relative) concentrations. The types which are nowadays most common are quadrupole mass spectrometers [Quad-MS] and time-of-flight mass spectrometers [TOF-MS].

(iv) Optionally further separate assemblies for transferring the ions from one assembly into the next, e.g. for accelerating, guiding or focusing the ions, for example acceleration distances, ion guides, ion lenses or ion funnels.

(v) Further components and assemblies that are necessary for the operation, e.g., valves, pumps, power supply means, in particular, e.g., for applying voltages to electrodes, etc.

There are also CI mass spectrometers which do not need a separate primary ion source (assembly (i)) in that the primary ions are generated in situ in the reaction chamber, e.g., by means of Penning ionization or by means of ionizing radiation.

PTR mass spectrometry and in general CI mass spectrometry are described, for example, in Ref. /1/, AT 001637 U1 (Lindinger and Hansel) and the references cited therein. Further descriptions of PTR mass spectrometry can be found i.a. in Ref. /2/, A. Hansel et al., International Journal of Mass Spectrometry and Ion Processes, 149/150 (1995) 609-619 and in Ref. /3/, A. Jordan et al., International Journal of Mass Spectrometry, vol. 286 (2009) 32-38.

The present invention relates to assembly (ii) ("reaction chamber") and the method steps taking place in this reaction chamber. In the relevant patent and technical literature, several different terms for this reaction chamber can be found, for example "reaction or ionization area", "reaction or ionization cell", or in cases in which the primary and product ions are drifting through the sample gas in a manner driven by electric fields also "drift tube or region or area".

The most simple form of a CI reaction chamber is the so-called "selected ion flow tube" [SIFT] as shown, e.g., in Ref. /4/, N. G. Adams and D. Smith, International Journal of Mass Spectrometry and Ion Processes, vol. 21 (1976), 349-359. Here, the primary and product ions are transported to the exit of the reaction chamber solely by the sample gas flow. This embodiment is disadvantageous on the one hand in that on their way in the direction towards the exit of the reaction chamber, ions diffuse in an unhindered manner towards the chamber wall and get lost there. Moreover, it is disadvantageous that in case, e.g., water vapor is present in the sample gas, clusters are formed of the primary ions and water molecules, and with the clustered primary ions the CI process in most cases can no longer take place as desired: For example, the analyte $C_6H_6$ (benzene) is ionized by the primary ion $H_3O^+$ but not by the primary ion cluster $H_3O^+ \cdot H_2O$.

A solution for reducing such undesired cluster formations are reaction chambers configured as so-called drift tubes as shown, e.g., in the above-mentioned Ref. /2/, A. Hansel et al. (1995). Here, the reaction chamber comprises a plurality of coaxial ring-shaped electrodes arranged along an axis in a spaced-apart manner. These ring-shaped electrodes surround the reaction volume of the reaction chamber in which the primary ions react with the sample gas and product ions are generated. A DC voltage is applied to each of the ring electrodes, wherein there is a potential difference between neighboring ring electrodes which accelerates the ions axially in the direction towards the exit of the reaction chamber. By the randomized collisions of the ions with the neutral particles of the sample gas, an ion-specific average drift speed and thus an ion-specific average collision energy are adjusted, the values of which depend on the pressure and the composition of the sample gas and the local electric field strength. By the DC voltages applied to the ring electrodes, it is possible to supply the resulting ion clusters with so much average kinetic energy that most of them fall apart again upon subsequent collisions with neutral sample gas particles which are not accelerated by the electric field. However, the average collision energy of the ions in the reaction chamber should be so low that the also undesired fragmentation of product ions is avoided as much as possible.

Such drift tubes in which static electric fields (DC fields) generated by ring electrodes drive ions in the axial direction towards the exit of the reaction chamber are particularly disadvantageous in that the acceleration of the ions in the axial direction necessary for avoiding cluster formation reduces the duration of stay of the ions in the reaction chamber and thus reduces the reaction time available for the ionization process, leading to a reduction in the product ion yield. In the following, "product ion yield" means: The ratio between product ions quitting the reaction chamber per time unit and the number of primary ions fed in per time unit. The product ion yield therefore is a measure of the ionization efficiency of the CI reaction chamber and has a decisive influence on the sensitivity of the CI mass spectrometer.

A further disadvantage of such drift tubes driven by axial DC fields is the fact that the ions are not guided transversely with respect to the axis and/or are not focused towards the axis, so that they diffuse away from the axis in an unhindered manner and therefore only a fraction of the ions passes through the exit orifice of the reaction chamber, which in turn reduces the product ion yield.

A possibility of guiding the ions also transversely with respect to the axis and/or of focusing them towards the axis in this ring-shaped electrode topology is to apply to the ring electrodes also AC voltages in addition to the DC voltage, as described, e.g., in Ref. /5/, S. Barber et al., Analytical Chemistry, 2012, vol. 84, 5387-5391 or in Ref. /6/, U.S. Pat. No. 6,107,628 (Smith and Shaffer). RF-AC voltages (i.e. AC voltages in the radio frequency range of about 100 kHz to about 100 MHz) are applied to the ring electrodes, said voltages being phase-shifted by 180° between two neighboring electrodes. These RF-AC voltages generate an effective potential which focuses the ions towards the axis and thus prevents ions from diffusing towards the chamber wall or towards the electrodes and from getting lost there or from being re-neutralized. DC voltages can be additionally superimposed in order to transport the ions towards the exit of the reaction chamber.

A disadvantage of such so-called ion lenses and ion funnels consisting of ring-shaped electrodes and being driven by RF-AC voltages is in particular the fact that the collision energies of the ions vary considerably in terms of time and position, because on the one hand the RF field oscillates about the value zero at every position and on the other hand the amplitude of this oscillation varies considerably along the axis. Thus, it is not possible to adjust an average collision energy which is optimum with respect to avoiding the formation of clusters and fragmentation and which should ideally be as constant as possible within the entire reaction volume in terms of time and position.

A further known possibility of guiding the ions in the reaction chamber transversely with respect to their transport direction and/or of focusing them towards the axis is using quadrupoles, hexapoles, oktopoles, etc. for guiding the ions. In this connection, an RF-AC voltage is applied to an even number of rod electrodes arranged in parallel to the axis and symmetrically around the reaction space, said voltage being phase-shifted by 180° between two neighboring rod electrodes and phase-shifted by 0° between two opposing rod electrodes. Such arrangements—in the following referred to as "2-phase multipoles"—generate an effective potential which focuses the ions towards the axis. This effective potential is generated by an interaction of the oscillating RF field with the randomized collisions of the ions with the neutral particles of the carrier gas which acts like a buffer gas.

A disadvantage of such 2-phase multipoles is the fact that on the axis the electric field is always zero Volt per centimeter [V/cm] since the fields of the respective opposing rod electrodes cancel each other out. This means that by means of the fields generated by such 2-phase multipoles, the average collision energy of the ions close to the axis, i.e. the place at which most ions are present because of the focusing, is not increased, so that an undesired formation of clusters cannot be reduced. Remote of the axis of symmetry of such 2-phase multipoles, the absolute value of the electric field vector oscillates between zero V/cm and a maximum value $E_{max}(r)$, which depends on the radial distance r from the axis. This leads to the same problems as those described above: It is not possible to adjust an average collision energy that is optimum with respect to avoiding the formation of clusters and fragmentation.

Concerning the prior art, reference is also made to the following documents:

AT 001637 U1 (Lindinger [AT]), 1997 Jul. 25
A. Hansel et al., Int. Journal of Mass Spectrometry and Ion Processes 149/150 (1995), pages 609-619
A. Jordan et al., Int. Journal of Mass Spectrometry 286 (2009), pages 32-38
EP 1 566 829 A2 (Hansel [AT], Wisthaler [AT]), 2005 Aug. 24
AT 406 206 B (Lindinger [AT] et al.), 2005 Mar. 27
AT 403 214 B (Ionentechnik GmbH [AT]), 1997 Dec. 29
S. Barber et al., Analytical Chemistry 84 (2012), pages 5387-5319
R. R. Julian et al., J. Am. Soc. Mass Spectrom. 16 (2005), pages 1708-1712
U.S. Pat. No. 6,107,628 A (Smith [US] et al.), 2000 Aug. 22
U.S. Pat. No. 6,674,071 B2 (Franzen [DE], Brekenfeld [US]), 2003 Jul. 24
DE 100 10 902 A1 (Bruker Daltronic GmbH [DE]), 2001 Sep. 20
US 2003/0136905 A1 (Franzen [DE], Brekenfeld [US]), 2003 Jul. 24
DE 10 2011 088 874 A1 (Thermo Fisher [DE]), 2012 Jul. 5
U.S. Pat. No. 5,811,800 A (Franzen [DE], Schubert [DE]), 1998 Sep. 22
U.S. Pat. No. 5,572,035 A (Franzen [DE]), 1996 Nov. 5
WO 2012/12370 A2 (Micromass UK Limited [GB]), 2012 Sep. 20
N. G. Adams and D. Smith, International Journal of Mass Spectrometry and Ion Processes, 21 (1976), pages 349-359
US 2008/0164409 A1 (Schulz [US] et al.), 2008 Jul. 10
WO 2010/141776 A2 (Varian Inc. [US]), 2010 Dec. 9
US 2005/0258354 A1 (Baba [JP] et al.), 2005 Nov. 24
US 2008/0203287 A1 (Crawford [US]), 2008 Aug. 28
DE 195 17 507 C1 (Bruker-Franzen Analytik GmbH [DE]), 1996 Aug. 8

SUMMARY

It is the object of the invention to provide a method and an apparatus as mentioned above, which improve the described disadvantages of the prior art, in particular by improving the product ion yield by an improved reduction in undesired cluster formation on the one hand and undesired fragmentation on the other hand. This object is achieved by the features of the claims.

The present invention deals with improving methods and apparatuses for the chemical ionization [CI] of a gas mixture or sample gas, wherein said gas mixture comprises at least one main component or carrier gas and one or more reactant gases or analytes which are in most cases present in very small concentrations. The mentioned ionization process is performed such that from non-ionized atoms or molecules of the reactant gases product ions are generated by reactions with primary ions which are additionally introduced into the gas mixture.

Like in most methods and apparatuses for the chemical ionization, also in the present invention the sample gas and the primary ions are introduced into a reaction volume (1) in which the CI processes take place and which has the following topology:

The surface of this reaction volume (1) comprises a first top surface (2), a second top surface (3) and a lateral surface (4) extending between these two top surfaces.

An axis—in the following referred to as central line (5)—passes through the reaction volume and extends from the first top surface (2) to the second top surface (3) and runs completely within the reaction volume (1), so that it is possible to define at each point of the reaction volume (1) an axial direction extending in parallel to the central line (5) and a radial direction and a radial plane extending orthogonally with respect to the central line (5).

It should be clarified that the terms reaction volume (1), first top surface (2), second top surface (3), lateral surface (4) and central line (5) do not mean really existing components of an apparatus but (abstract) geometrical objects for describing topological characteristics of the prior art and the present invention.

In most reaction chambers according to the prior art, the reaction volume (1) is substantially rotationally symmetrical, i.e. cylindrical or cone-shaped. The central line (5) is on the straight axis of rotational symmetry of the cylinder. However, also designs of the reaction volume which are different from the rotationally symmetrical shape are possible, sometimes advantageous and provided in accordance with the invention, for example designs with bent or S-shaped central line, for example in order to fade out undesired radiation from the primary ion source on its way through the reaction space and prevent it from entering the assemblies downstream of the reaction chamber (e.g. mass spectrometer).

This prior art topology of the reaction volume (1), in which an axial and a radial direction is defined, is due to the fact that the primary ions are in most cases introduced through the first top surface (2) into the reaction volume (1) and the product ions (and also the remaining primary ions) are transported through the reaction volume by means of a gas flow and/or by means of static electric fields in the axial direction until they leave the reaction volume through the second top surface (3) towards the exit of the reaction chamber. As stated above, focusing the ions towards the central line (5), i.e. guiding them radially, is advantageous and desirable but not absolutely necessary.

In reaction volumes having the presently described topology, the axial direction is thus the transport or drifting direction of the ions, and the radial direction orthogonal thereto is the direction in which the ions are guided or focused towards the central line (5), optionally by means of effective potentials generated by means of RF fields.

The above detailed discussion of the advantages and disadvantages of the prior art leads to the following (competing) criteria relating to the optimization of methods and apparatuses for the chemical ionization according to the invention, which use reaction volumes having the topologies as described herein:

(A) For reducing undesired cluster formation, generated ion clusters are accelerated so much by means of an electric field that they fall apart again upon subsequent collisions with sample gas particles which are neutral and which thus are not accelerated by the electric field.

(B) However, the electric field should not supply the product ion ensemble with so much kinetic energy (i.e. average collision energy) that fragmentation occurs upon collisions with neutral sample gas particles.

(C) (A) and (B) lead to an "optimum window" for the electric field strength or even an optimum field strength larger than zero, which should be as constant as possible in terms of time and position, at least in the area of the reaction volume in which the ion density is the highest. According to the prior art, this suggests the use of static fields (DC fields, which, however, are disadvantageous regarding the product ion yield, as evident from the following explanation as to criterion (D).

(D) For achieving a high product ion yield, the available reaction time, i.e. the duration of stay of the primary ions within the reaction volume, should be long. Strong DC fields for fulfilling criterion (C) are therefore disadvantageous regarding the product ion yield because they transport the primary ions quickly out of the reaction volume and thus reduce the available reaction time.

(E) Guiding or focusing the ions along the central line by means of effective potentials generated by RF-AC fields is advantageous and desirable, but in all solutions according to the prior art runs contrary to criterion (C) which requires a field strength being constant in terms of time (and ideally also in terms of position).

The invention provides a method of the above-mentioned kind, which improves the disadvantages of the prior art, in particular in that it fulfills the above optimization criteria better than the prior art. According to the invention, this is achieved by the characterizing features of claims 1 to 5.

It is much easier to clarify and define the principle and the advantages of the method according to the invention by explaining them first on the basis of the features of claim 1 and then further on the basis of the features of dependent claim 5 instead of explaining them on the basis of the features of claim 1 alone. The inventive considerations and advantages which form the basis of claims 1 to 4 alone are then additionally defined and explained in the further description of the invention. These further explanations also clearly show that also embodiments according to claims 1 to 4 are based on the same inventive principle and are thus also comprised by the invention.

The method according to the invention can further comprise the following method steps:

Step A: Accelerating the ions (primary ions, generated product ions and possibly also generated ion clusters) in the reaction volume (1) by means of a temporally periodic electric field E(x,t), wherein E(x,t) has a radial field vector component $E_r(Z,t)$ which, at all points {Z} lying on the central line (5), is orthogonal with respect to this central line (5) and which rotates periodically, making exactly a 360° rotation in the radial plane during the cycle duration T, and the absolute value $|E_r(Z,t)|$ of $E_r(Z,t)$ is unequal to zero in preferably more than 80% of the times lying within a cycle duration T, particularly preferably is at all times unequal to zero, particularly preferably is constant or almost constant, wherein E(x,t) has an axial field vector component $E_{axi}(Z,t)$ which, at all points {Z} lying on the central line (5), is parallel with respect to the central line (5) and the absolute value $|E_{axi}(Z,t)|$ of which is preferably smaller than the absolute value of the rotating radial component $|E_r(Z,t)|$, preferably clearly smaller or zero, wherein t is the time, x is a position vector, for example having the Cartesian coordinates (x, y, z), Z is the position vector of a point lying on the central line (5), {Z} is the set of all position vectors Z belonging to the central line (5), and T is the cycle duration of a 360° rotation of $E_r(Z,t)$, and optionally wherein at all times t and at all points {Z} lying on the central line, the absolute value $|E_r(Z,t)|$ of the rotating field vector $E_r(Z,t)$ is unequal to zero and almost constant, i.e. deviates by a maximum of ±10% from its average value $E_0$ being averaged in terms of time and location, preferably is constant, and wherein the absolute value of the axial field component $|E_{axi}(Z,t)|$ is at all times negligibly small relative to the radial component, preferably equal to zero, i.e. $|E_{axi}(Z,t)|\approx 0$ and thus $E(Z,t)\approx E_r(Z,t)$, and $|E(Z,t)|\approx|E_r(Z,t)|=E_0\pm 10\%$.

In other words, in the method according to claim 5, which is back-referenced to claim 1, a temporally periodic electric field E(x,t) is applied, which has the following property at all points {Z} of the central line: The field vector E(Z,t) has no decisive axial component, is therefore orthogonal with respect to the central line, rotates periodically and has an almost constant, i.e. preferably constant absolute value $E_0$. The less strict requirement that the absolute value $E_0\pm 10\%$ is not necessarily strictly constant is due to the technical feasibility limits related with the generation of such E-fields: The preferred frequencies lie in the MHz range, and the preferred amplitudes of the AC voltages lie in the kV range. Based on these specifications it is sometimes very complicated or hardly practicable to generate completely "clean", i.e. distortion-free sinusoidal voltages. More detailed statements in this regard can be found below in the description of the apparatus of the present invention.

It results from the known properties of electric fields and from basic considerations as to continuity and symmetry that this rotating E-field must have the same properties also in a vicinity of the central line, i.e. within a central volume (closely) surrounding the central line: The field vector rotates with the same cycle duration or frequency orthogonally with respect to the central line (i.e. in the radial plane) and its absolute value $E_0$ is at least almost constant. (Further details in this regard can be found below in the explanations as to FIG. 2.)

The acceleration of the ions by means of an E-field having these properties has the following effects and advantages:

(I) The ions are accelerated with an almost constant field strength always in the radial direction, so that it is possible to fulfill optimization criterion (C) [cluster formation versus fragmentation] following from optimization criteria (A) and (B) without violating optimization criterion (D) [duration of stay or reaction time] because the primary ions are not transported by the applied field quickly axially towards the exit of the reaction chamber. In other words, it is thus possible to accelerate the ions "optimally" in accordance with criterion (C) without reducing the reaction time of the primary ions because the radial acceleration direction of the ions is decoupled from the transport towards the exit of the reaction chamber along the central line. This is the central principle of the invention.

(II) When using a suitable rotational frequency of the field vector, the ions are not driven out of the reaction volume radially towards the lateral surface, which would violate criterion (D) [duration of stay or reaction time], but quite the contrary applies: In interplay with randomized collisions of the ions with the neutral carrier gas acting like a buffer gas, the quickly rotating, spatially inhomogeneous E-field generates an effective potential which focuses the ions towards the central line, so that also optimization criterion (E) [focusing] is fulfilled.

(III) The above item II. (focusing to the central line) has additionally a positive effect on the fulfillment of criterion (C) [cluster formation versus fragmentation], which requires acceleration of the ions at a constant, "optimum" field strength because due to this focusing, most of the ions are in the central volume (closely) surrounding the central axis, and a spatial inhomogeneity of the field strength therefore does not play an important role.

(IV) If no or only a weak effective potential which focuses the ions towards the central line is generated—as this may be the case in some embodiments of the invention—the ions are also then not driven quickly radially out of the reaction volume by the rotating field vector: If the rotational frequency is sufficiently high (e.g. in the MHz range), the E-field cannot drive the ions, which are slowed down and thus have a strongly reduced mobility because of the many randomized collisions with the carrier gas acting like a buffer gas, to the wall of the reaction chamber before the E-field already points (half a cycle duration later) in the counter direction, i.e. away from the chamber wall. In other words and simply speaking, the ions are not driven radially out of the reaction volume because the direction of acceleration by the E-field is always quickly rotating and, therefore, no direction in which the ions, which are slowed down by the carrier gas and thus are less mobile, are driven is preferred.

These explanations make clear that advantages are already achieved if not so strict demands are made on the periodically rotating E-field than in accordance with claim 5 (constant absolute value and omission of an axial field component). A periodically rotating radial component $E_r(Z,t)$ in any case supplies the ion ensemble with kinetic energy which is useful for avoiding cluster formation without accelerating the ion transport through the reaction volume and thus reducing the reaction time in a disadvantageous manner.

It is shown below that E-fields according to the invention can also be generated by means of phase-shifted square wave voltages. The preferred frequencies are in the MHz range, and the necessary electrical voltages reach into the kV range. With these frequencies and voltages, an ideal square wave signal cannot be made, and when generating the E-field according to the invention, it might happen that the rotating field vector $E_r(Z,t)$ also becomes zero during some times during a rotation due to a signal shape being different from a perfect rectangle. In the (predominant) times in which $E_r(Z,t)$ is not zero, it has the advantageous effect according to the invention as described above.

In many cases it is advantageous if the applied E-field has also an axial component $E_{axi}(Z,t)$, preferably with moderate but constant absolute value. This axial component can serve for transporting the ions towards the exit of the reaction volume, in particular in case there is no adequate gas flow. Vice versa, if there is a strong gas flow, this axial component can serve for increasing the duration of stay of the ions within the reaction volume in an advantageous manner in that this axial component is directed contrary to the gas flow.

The prior art does not include any method which suggests the presently suggested E-field topology which is advantageous in several aspects and comprises a periodically rotating field vector for optimizing the chemical ionization of a sample gas.

E-fields whose rotating radial component $E_r(Z,t)$ has an absolute value $|E_r(Z,t)|$, which varies at all points {Z} on the central line (5) by at most 50% of its maximum value $E_{max}(Z)$ in more than 80% of the times lying within a cycle duration T, i.e. lies in the interval $[0.5*E_{max}(Z), E_{max}(Z)]$, are advantageous and preferred (e.g. claim 2). This improves the fulfillment of the optimization criteria discussed above.

Moreover, E-fields in which the absolute value $|E_r(Z,t)|$ varies over at least 80% of the length of the central line (5) by at most 50% of its maximum value are preferred and advantageous (e.g. claim 3). This further improves the fulfillment of the optimization criteria discussed above.

Furthermore, E-fields are particularly preferred and advantageous which are characterized in that the rotation of the radial field vector component $E_r(Z,t)$ substantially corresponds to a harmonic circular motion, i.e. that, when shown in Cartesian coordinates (X,Y) being at the respective point Z orthogonal to the central line (5), $E_r(Z,t)$ meets the following equation:

$$E_r(Z,t)=u_x \cdot [A_x(Z,t) \cdot \sin(\omega t+\Phi_0)]+u_y \cdot [A_y(Z,t) \cdot \cos(\omega t+\Phi_0)],$$

wherein $u_x$ is the unit vector of the X-coordinate and $u_y$ is the unit vector of the Y-coordinate, $\omega$ is the angular frequency of rotation, $\Phi_0$ is a global phase offset, and wherein the absolute value $|E_r(Z,t)|$ varies by at most ±10%, preferably is constant at all times, i.e. $|E_r(Z,t)|=E_0 \pm 10\%$, wherein $E_0$ is a constant (claim 4). This further improves the fulfillment of the optimization criteria discussed above.

As already discussed in detail above, in particular E-fields are particularly preferred and advantageous which are characterized in that the absolute value $|E_r(Z,t)|$ of the rotating field vector $E_r(Z,t)$ is unequal to zero and almost constant at all times t and at all points {Z} lying on the central line, i.e. deviates by at most ±10% from its average value $E_0$ being averaged in terms of time and location, and wherein the axial field component $E_{axi}(Z,t)$ is equal to zero at all times, i.e. $E(Z,t)=E_r(Z,t)$ and $|E_r(Z,t)|=E_0 \pm 10\%$ (claim 5).

Here it also becomes clear why it is not necessary for the clarity of the disclosure of the invention to clarify in the claims where the central line exactly extends spatially with respect to the top surface and lateral surfaces (e.g. by a definition such as "the central line extends from the center of the first top surface to the center of the second top surface"). The top surfaces and lateral surface and the central line are no really existing components of an apparatus but abstract geometrical objects for describing the topology of the reaction chamber and of the E-field characterizing the invention. The central line thus extends implicitly at the position where the E-field according to the invention is applied and/or at the position where the E-field has the properties belonging to the central line and/or is formed "automatically" virtually at the position where the field having the properties defined in accordance with the invention is applied. This argumentation analogously also applies to the apparatus according to the invention which is disclosed in the following.

The invention provides an apparatus of the kind mentioned at the beginning, which improves the disadvantages of the prior art, in particular by providing an apparatus by means of which, e.g., also the advantageous method according to the invention can be carried out. In particular, according to the invention it is possible to generate electric fields $E(x,t)$ having the characterizing features of the method claims 1 to 5 within the reaction volume. In accordance with the invention, this is achieved in particular by the characterizing features of claims 6 to 14.

The mentioned apparatus includes—like most reaction chambers according to the prior art used for the chemical ionization—a reaction area or reaction volume (1), wherein the surface of this reaction volume comprises a first top surface (2), a second top surface (3) and a lateral surface (4) extending between the two top surfaces (2, 3) and wherein a central line (5), which extends from the first top surface (2) to the second top surface (3) and completely runs within the reaction volume (1), so that it is possible to define within the reaction volume (1) an axial direction extending in parallel to the central line (5) and a radial direction and a radial plane being orthogonal to the central line (5).

It should be clarified once again that the terms reaction volume (1), first top surface (2), second top surface (3), lateral surface (4) and central line (5) do not mean really existing components of an apparatus but (abstract) geometrical objects for describing topological characteristics of the prior art and of the present invention.

The mentioned apparatus further comprises three or more preferably rod-shaped electrodes (6), i.e. N electrodes (6), wherein N is an integer larger than or equal to three, wherein each of these N≥3 electrodes (6) is configured and arranged such that it extends from the boundary of the first top surface (2) to the boundary of the second top surface (3) and snuggles from the outside to the reaction volume (1), i.e. that it contacts the lateral surface (4) along its overall extension being tangent to it from the outside.

The mentioned apparatus further comprises an AC voltage source which can be electrically connected to each of the N≥3 electrodes (6).

The mentioned apparatus is characterized in that the AC voltage source is configured such that a periodic AC voltage (i.e. a temporally periodic voltage) $U_i(t)$ can be applied to each of the N≥3 electrodes (6), wherein $U_i(t)$ is the AC voltage at the i-th electrode, wherein the AC voltages $U_1(t)$ to $U_N(t)$ each have the same cycle duration T or the same frequency $f=1/T$, wherein, however, all AC voltages $U_i(t)$ have a different phase position $\varphi_i$ between 0° and 360°, i.e. each voltage $U_{i>1}(t)$ is temporally shifted with respect to the first voltage $U_1(t)$ by the fraction $\Delta t_i = (\varphi_i/360°) \cdot T$ of the cycle duration T, wherein, when the electrodes (6) are numbered consecutively along the boundary of a top surface (2, 3) in a sense of rotation, the phase positions $\varphi_i$ and $\Delta t_i$ are arranged in ascending order, i.e.

$$\varphi_1=0°<\varphi_2<\ldots<\varphi_i<\ldots<\varphi_N<360°, \text{ and}$$

$$\Delta t_1=0<\Delta t_2<\ldots<\Delta t_i<\ldots<\Delta t_N<T.$$

In other words, at least three electrodes extend from the boundary of the first top surface (2) along the lateral surface (4) right up to the boundary of the second top surface (3), and AC voltages having phase positions ascending in one sense of rotation are applied to said electrodes. Thus, it is possible to generate within the reaction volume a periodically rotating electric field which has the characterizing features of the electric field of the method according to the invention and as a consequence this leads to the advantages described above in detail.

Particularly preferable are electrode arrangements which are at any point of the central line (5) rotationally invariant at a rotation by 360°/N, wherein N is the number of electrodes, and AC voltages whose phase positions are $\varphi_i=[(i-1)/N] \cdot 360°$, wherein i is the i-th electrode.

However, it is explicitly pointed out that also differing electrode arrangements and phase positions lead to the inventive effect that a periodically rotating E-field is generated in the reaction volume. The only requirement is that at least three electrodes as described extend along the lateral surface and are energized in a sense of rotation with ascending phase positions. However, rotation of the radial field component is in this case generally not "harmonic" in the meaning of a circular motion with constant angular frequency, but it takes place and leads to the advantages according to the invention.

In the following, the apparatus according to the invention is referred to as "N-phase multipole", i.e. for example in case three electrodes are present as "N-phase tripole". RF-multipoles of the prior art in which, as discussed above in detail, the electrodes are only energized with two phase positions (0° and 180°) and which thus do not generate a rotating E-field and in which furthermore the E-field is always zero on the central line are referred to as "2-phase multipoles".

BRIEF DESCRIPTION OF THE DRAWINGS

Further details and advantages of the invention are explained in the detailed description on the basis of the enclosed drawings in which.

DETAILED DESCRIPTION

Figure 1:
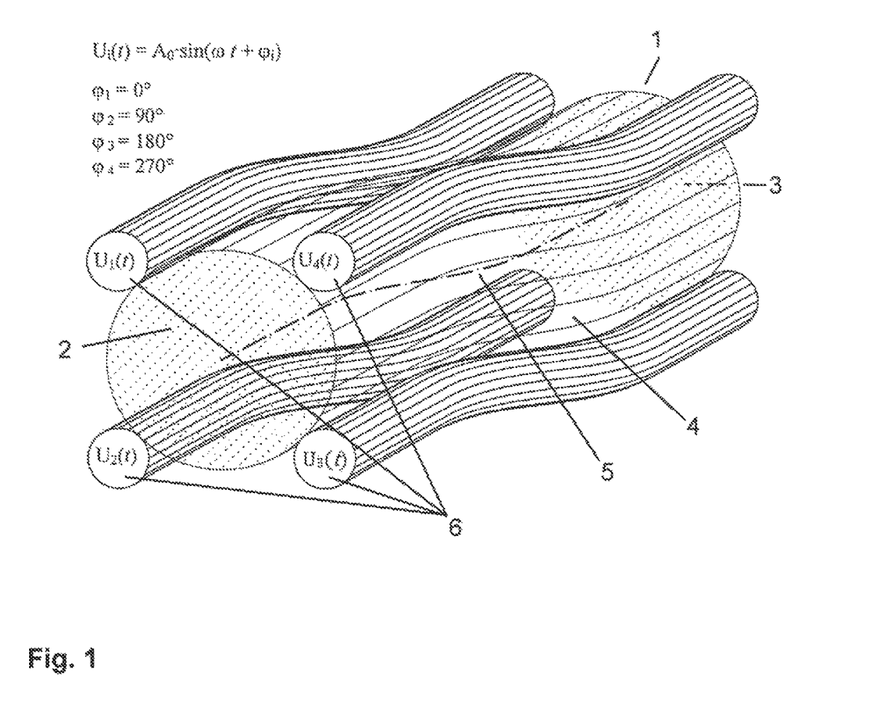
FIG. 1 shows a rough schematic oblique view of an embodiment of the apparatus according to the invention comprising four symmetrically arranged electrodes (6)

FIG. 1 shows a rough schematic oblique view of an embodiment of the apparatus according to the invention comprising four schematically arranged electrodes (6) which are energized by four sine voltages $U_i(t)$ having the phase positions 0°/90°/180°/270°. The Figure shows the electrodes (6) as well as the reaction volume (1) with the two top surfaces (2, 3), the lateral surface (4) and the central line (5). The AC voltage source and the electrical connections to the electrodes are not shown in FIG. 1 for the sake of clarity. The central line (5) is bent in an S-shape and the cross-section through the reaction volume (1) is circular with constant radius along the entire central line (5).

The embodiment shown in FIG. 1 and having a central line being bent in an S-shape is particularly advantageous in that undesired radiation escaping the primary ion source can easily be blocked on its (straight) path through the reaction volume, e.g. by using an aperture at the top surface (3). This is advantageous because it can be easily avoided that undesired background radiation enters the analyzer/detector unit downstream of the reaction chamber.

FIG. 1 clearly shows that the four electrodes (6) are energized in accordance with the invention with AC voltages whose phase positions ascend in one sense of rotation. The shown sense of rotation is the counter-clockwise direction.

Applying sine voltages with the shown regular phase positions (0°/90°/180°/270°) to the shown electrode arrangement being symmetrical in each radial plane is particularly advantageous because the radial field vector component $E_r(Z,t)$ in this case performs a harmonic circular motion with constant absolute value and constant angular frequency on the central line. But also other, less symmetrical arrangements of the electrodes and/or other signal shapes and phase positions of the AC voltages are provided in accordance with the invention and sometimes advantageous. For example, less symmetrical arrangements and phase positions lead to the fact that the absolute value $|E_r(Z,t)|$ changes during a rotation, i.e. is not constant. For example, this is advantageous if it is intended to accelerate the ions in a sample gas having many different analyte components not with a constant field strength but in a broader energy band.

Figure 2A:
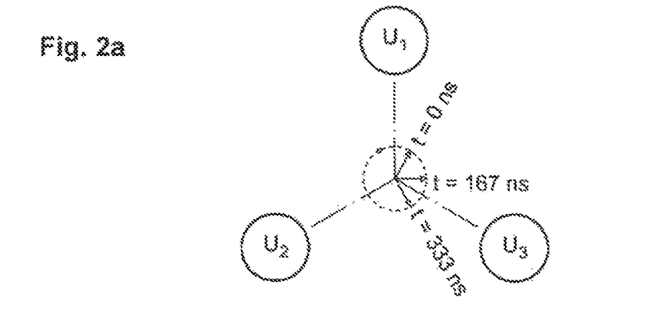
FIGS. 2*a*-*c* show rough schematic sections through an N-phase tripole (FIG. 2*a*) and an N-phase quadrupole (FIGS. 2*b* and 2*c*) according to the invention as well as the respective temporal course of the rotating E-field vector $E_r(Z,t)$.
Figure 2B:
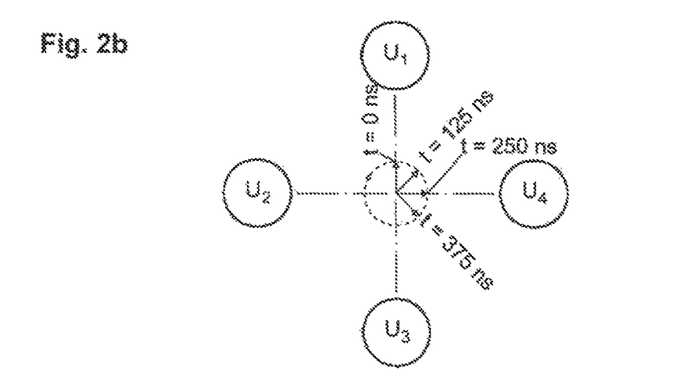
Figure 2C:
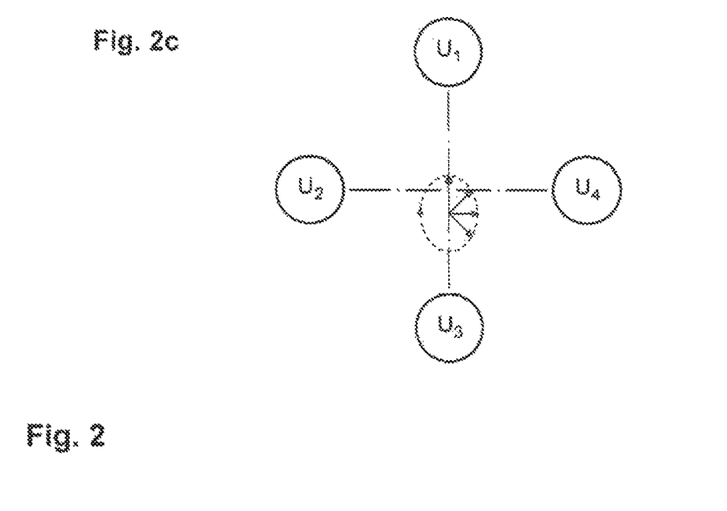

FIGS. 2a-c show rough schematic sections through an N-phase tripole (FIG. 2a) and an N-phase quadrupole (FIGS. 2b and 2c) according to the invention as well as the respective temporal course of the rotating E-field vector $E_r(Z,t)$. For the sake of clarity, these Figures do not contain reference numbers because it is clearly visible that the Figures show sections through the electrodes (6) to which AC voltages $U_i(t)$ are applied.

FIG. 2a shows the situation in an N-phase tripole according to the invention: When this symmetric electrode arrangement is energized with three sine voltages having the phase positions 0°, 120° and 240°, the E-field vector $E_r(Z,t)$ makes a harmonic circular motion with constant absolute value and constant angular frequency on the central line (5). The Figure shows a rough schematic view of the temporal course of the E-field vector $E_r(Z,t)$ assuming that sine voltages having a frequency of 1 MHz are applied.

FIG. 2b shows the same as FIG. 2a but for an N-phase quadrupole according to the invention, i.e. an embodiment with four electrodes to which sine voltages having the phase positions 0°, 90°, 180° and 270° are applied.

FIG. 2c shows the same as FIG. 2b, wherein, however, the temporal course of the E-field vector $E_r(x,t)$ at a point x away from the central line is shown. It is clearly evident that the field vector rotates periodically, that its absolute value never becomes zero and that its absolute value changes only moderately during rotation.

In case a gas mixture of ions and neutral carrier gas particles is used, all N-phase multipoles shown in FIG. 1 and FIG. 2 generate an effective potential which focuses the ions towards the central line. The inhomogeneity of the field away from the central line shown in FIG. 2c is of minor importance because due to the focusing effect of the effective potential most of the ions are present in the close vicinity of the central line where the absolute value of the rotating E-field changes only little or is almost constant.

Figure 3:
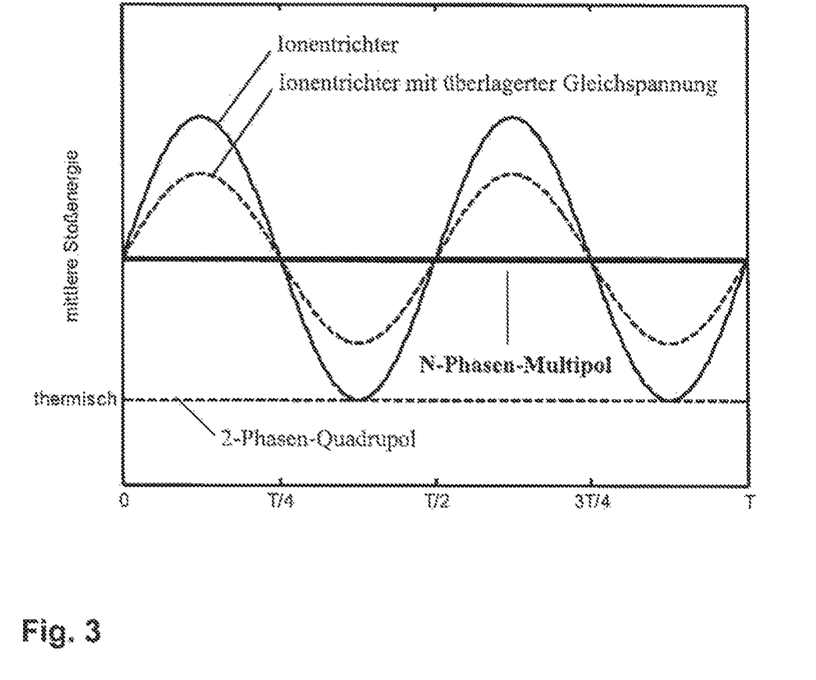
FIG. 3 shows a rough schematic view of the qualitative course of the average collision energy between primary ions and neutral carrier gas particles on the central line depending on time within a cycle duration T for an RF ion funnel without and with superimposed DC voltage, for a 2-phase quadrupole (=prior art) as well as for an N-phase multipole according to the invention.

FIG. 3 shows a rough schematic view of the qualitative course of the average collision energy between primary ions and neutral carrier gas particles on the central line depending on time within a cycle duration T for an RF ion funnel without and with superimposed DC voltage, for a 2-phase quadrupole (=prior art) as well as for an N-phase multipole according to the invention.

As mentioned in the above chapter "prior art", the ion funnels of FIG. 3 are in the form of axially arranged ring electrodes to which alternately 0° and 180° phase-shifted RF-AC voltages and optionally additionally DC voltages are applied and which thus generate an oscillating AC field in the axial direction and, in case additionally a DC voltage is applied, additionally also generate a DC offset in the axial direction. FIG. 1 clearly shows that in reaction chambers being realized as ion funnel, the average collision energy of the ions oscillates strongly and thus an optimum and constant average collision energy of the ions cannot be achieved. The collision energy oscillates with twice the frequency of the applied AC voltage because the square of the electric field is the decisive value for the acceleration of the ions and thus for the collision energy. It is clearly evident that in the ion funnel without DC offset, the supply of collision energy again and again becomes zero, so that at these times the ions only have the average thermal collision energy. In the ion funnel with DC offset, the amplitude of the RF-AC voltage can be selected to be somewhat smaller, but nevertheless there are strong oscillations. Moreover, the DC offset is orientated axially along the central line and drives the ions, at the expense of the product ion yield, more quickly in the radial direction out of the reaction volume.

FIG. 3 also shows clearly that 2-phase quadrupoles of the prior art which are energized with RF-AC voltages do not accelerate the ions on the central line because for reasons of symmetry the electrical field at the central line is always zero. On the central line, i.e. at the place where most ions are present because of the focusing, the ions thus only have the average thermal collision energy and form clusters to an increasing degree. Away from the central line, the field oscillates without rotating, so that also the absolute value of the field strength oscillates. Achieving an optimum, preferably constant average collision energy for reducing cluster formation thus also becomes impossible away from the central line. There are also 2-phase multipoles in which also an axially-directed DC offset is superimposed for accelerating the ions, which, however, leads to the described disadvantage that the ions are driven more quickly out of the reaction volume.

FIG. 3 also shows clearly that in the N-phase multipole according to the invention the average collision energy on the central line is constant in terms of time, leading to all advantages already discussed in detail. This Figure shows an N-phase multipole according to FIG. 1 or 2 which, due to the symmetric design and the energizing with sine voltages having regular phase positions $\varphi_i=[(i-1)/N]\cdot 360°$ on the central line, generates a field vector $E_r(Z,t)$ rotating with harmonic circular motions and having a constant absolute value.

FIGS. 4a-h show oblique views of embodiments of the electrodes (6) according to the invention. For the sake of clarity, only the electrodes and the central line (5) (in dashed lines) are shown but not the surface of the reaction volume (1).

FIGS. 4e-h show embodiments with helical electrodes (6). When a gas mixture of ions plus neutral carrier gas particles is used, these embodiments generate an effective potential in the axial direction. This effective axial potential can be used in an advantageous manner for moderately transporting the ions through the reaction volume. The direction of this effective axial potential of helical electrodes depends on the sense of rotation of the applied AC voltages. Therefore, this effective potential can also be used for slowing down the ions relative to the sample gas flow in order to keep them a longer time in the reaction volume.

Figure 4A:
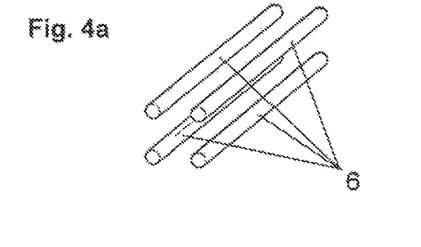
FIGS. 4*a*-*h* show schematic oblique views of embodiments of the electrodes (6) according to the invention.
Figure 4B:
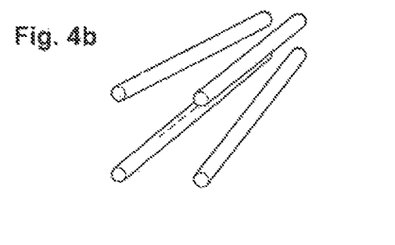

Also embodiments are advantageous in which the lateral surface tapers along the central line, as shown in FIGS. 4b and f. In such embodiments, in addition to the rotating radial E-field component, also a (moderate) field component $E_{axi}(Z)$ is generated which can also be constant in terms of time and thus makes an axial DC contribution which can be used advantageously for moderately transporting the ions through the reaction volume or for slowing down the ions relative to the sample gas flow. Moreover, tapering electrode configurations can be used, e.g., in an advantageous manner for focusing the ions towards an exit orifice.

Figure 4C:
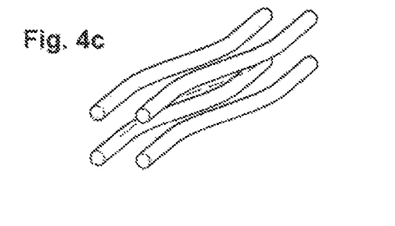

FIGS. 4c and g show embodiments in which the central line is bent in an S-shape. The advantages thereof have already been discussed above in detail. Of course also advantageous shapes of the central line differing from an S-shape are conceivable and intended in accordance with the invention.

Figure 4D:
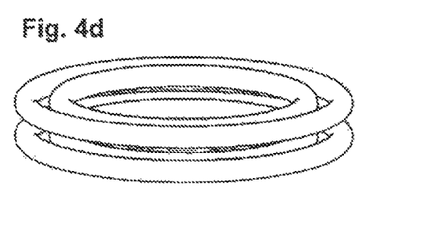
Figure 4E:
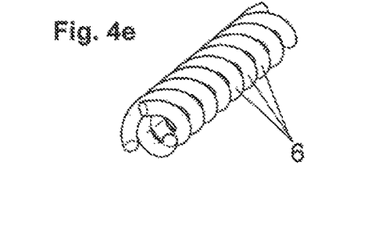
Figure 4F:
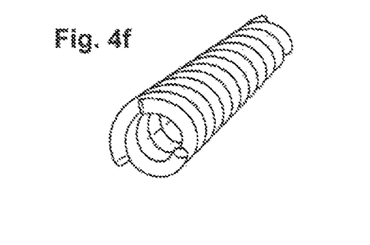
Figure 4G:
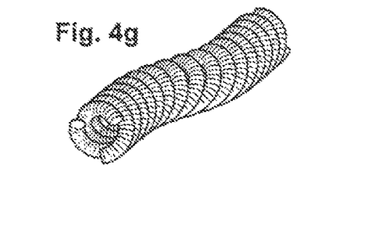
Figure 4H:
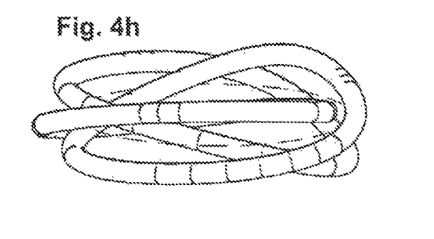

FIGS. 4d and h show special cases of a reaction volume according to the invention: The first top surface and the second top surface coincide in one surface and the reaction volume is closed so that the ions can, e.g., be kept for a very long time in the reaction volume. However, in this case it is necessary to provide suitable additional devices for introducing and removing the gas particles.

Of course also combinations of the designs of the electrode and/or the central line and the lateral side of the reaction volume shown in FIG. 4 are conceivable and provided in accordance with the invention, e.g. bent and tapering shapes, or, e.g., shapes non-tapering in one portion and tapering in a second portion as well as a plurality of further conceivable designs.

Of course also electrode designs differing from those shown in FIG. 4 are conceivable and provided in accordance with the invention, e.g. helices with varying thread or other free shapes extending from the edge of the first top surface (2) to the edge of the second top surface (3) and snuggling to the lateral surface (4) tangentially.

Figure 5:
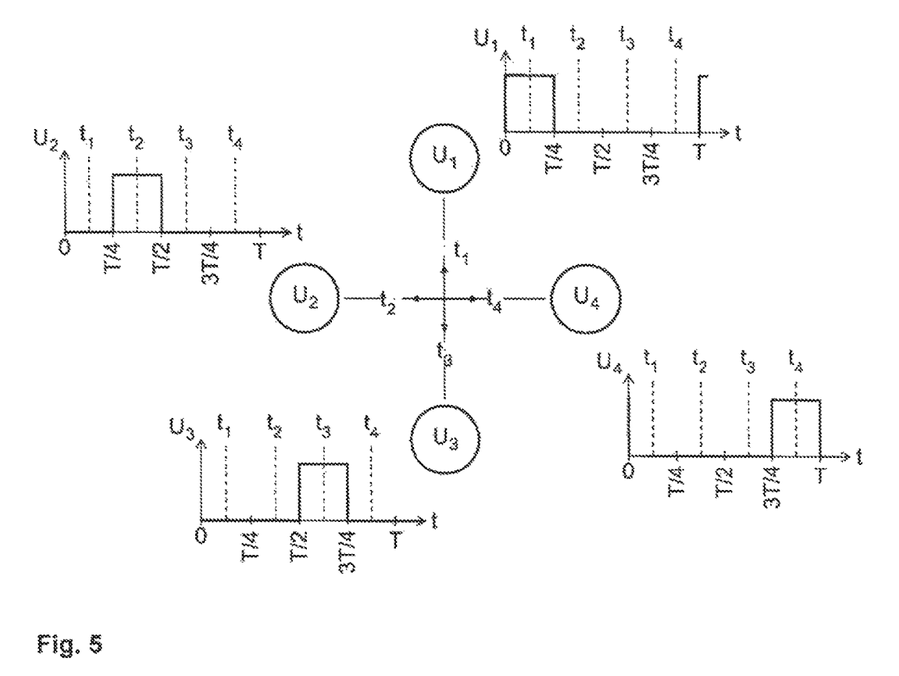
FIG. 5 shows a rough schematic section through an N-phase quadrupole according to the invention which is energized with phase-shifted square wave voltages having the pulse control factor of 1:4; the Figure also shows a rough schematic view of the square wave voltages applied to the electrodes (6) as well as the E-field vector $E_r(Z,t)$ at the four time points $t_1$ to $t_4$.

FIG. 5 shows a rough schematic section through an N-phase quadrupole according to the invention which is energized with phase-shifted square wave voltages having the pulse control factor of 1:4. The Figure also shows a rough schematic view of the square wave voltages applied to the electrodes (6) as well as the E-field vector $E_r(Z,t)$ at the four time points $t_1$ to $t_4$.

FIG. 5 clearly shows that at the time point $t_1$ a voltage is applied only to the first electrode and, therefore, the E-field vector is directed at this time point towards the first electrode. At the time point $t_2$ a voltage is applied only to the second electrode and, therefore, the E-field vector is directed at this time point towards the second electrode and so on. The E-field vector thus rotates so to say in a "jumping" manner in 90° steps, but its absolute value is constant. Generally speaking, with the following pulse control factors the absolute value of the E-field vector rotating in a "jumping" manner remains constant: The pulse control factor Q of the square wave voltage must meet the following equation:

$Q=(n/N):N$, wherein $N$ is the number of electrodes and $n$ is an integer between 1 and (1–$N$).

For example, a quadrupole according to the invention can be energized with the pulse control factors 1:4, 2:4 and 3:4 and—assuming a correct phase position of the square wave voltages—the absolute value of the E-field vector rotating in a "jumping" manner remains constant.

The preferred frequencies are in the MHz range, and the preferred voltages reach into the kV range. With such reference values, perfect square wave voltages cannot be achieved in a technical sense due to the limited cut-off frequency and slew rate. In square wave voltages which can be generated in a real manner and have a finite slew time it might be the case that in each time slot in which the square wave pulse is "handed over" from one electrode to the next there might be fluctuations in the absolute value of the field vector. However, as long as these time slots for "handing over" can be kept short as compared to the cycle duration T, the advantages according to the invention are still present by nature because the ions can at least most of the time be accelerated with the optimum field strength.

When configuring the reaction volume (1), i.e. when configuring and arranging the electrodes (6), which snuggle to the lateral surface (4), in accordance with the invention, the following dimensions and configurations are preferred, wherein the particularly preferred dimensions and configurations are due to the concrete requirements and specifications of the respective application:

Length [L] of the reaction volume along the central line (5):
L=approx. 5 mm to approx. 100 mm
Inner diameter [D] of the reaction volume (1), measured orthogonally to the central line (5):
D=1 mm to approx. 20 mm
Cross-Section of the Electrodes (6):
In order to avoid field peaks it is advantageous to avoid sharp edges in the electrode cross-section. The following cross-sections are particularly preferred:
circular or elliptical cross-sections, or segments thereof with rounded corners; circular cross-sections are, e.g., particularly preferable for optimizing a constant absolute value of the rotating E-field on the central line (5);
parabola segments with rounded corners, in particular for optimizing the homogeneity of the E-field and/or the effective potential in the entire reaction volume (1);
hyperbola segments with rounded corners, in particular for optimizing the homogeneity of the E-field and/or of the effective potential in the entire reaction volume (1);
also cross-sections which taper along the electrodes are provided and advantageous in accordance with the invention, in particular in tapering reaction volumes.

The following process parameters are particularly preferred in the chemical ionization carried out in accordance with the invention:

Gas pressure [p] of the sample gas in the reaction volume (1):
p=approx. 10 mbar to atmospheric pressure (1 bar), wherein high gas pressures are preferred for several reasons, in particular because they increase the product ion yield, but for avoiding cluster formation they require high electric field strengths with which technical feasibility limits might be occasionally reached. (In view of a more detailed explanation reference is made to "maximum amplitude" below.)

Concentration [conc.] of the reactant gases or analytes contained in the sample gas:
conc.=smaller than 10 ppbv (ppbv=parts per billion by volume), wherein also with concentrations in the sub-pptv range (pptv=parts per trillion by volume) a significant product ion yield can be achieved.

Maximum amplitude [$E_{max}$] of the radial component of the rotating E-field on the central line (5), wherein the optimum amplitude depends on the mixture of substances of the sample gas (cluster formation versus fragmentation of the analyte particles contained in the mixture of substances) as well as in particular on the gas pressure p: If the gas pressure p is high, the mean free path length of the gas particles is smaller, therefore the accelerated electric field must be accordingly larger to avoid cluster formation, so that the particles receive the necessary energy through the field between two collisions.
$E_{max}$=approx. 500 V/cm to approx. 10 kV/cm
Frequency f of the rotating E-field and of the AC voltages $U_i(t)$ applied to the electrodes, wherein the optimum frequency strongly depends on other process parameters such as, e.g., the gas pressure p as well as on the technical feasibility (see above: 10 kV/cm in the MHz range reaches technical feasibility limits):
f=approx. 100 kHz to approx. 100 MHz
Thus—depending on the above inner diameter D and depending on the technical feasibility—the following typical amplitudes [$U_0$] of the AC voltages applied to the electrodes (6) are:
$U_0$=approx. 50 V to approx. 10 kV
Signal shape of the AC voltages $U_i(t)$ applied to the electrodes (6):

As discussed above, particularly preferred are sinusoidal and square wave AC voltages. However, also different signal shapes are advantageous for some applications and provided in accordance with the invention, e.g.:

triangular or saw-tooth voltages, e.g. for selectively broadening the collision energy of the ion ensemble accelerated by the field;

additionally applied DC offsets, in particular also those changing along the electrodes (6) in that the electrodes are segmented or made from a resistive material; this allows the implementation of, e.g., an axially acting E-field component for transporting the ions in the direction of the exit of the reaction chamber;

additionally modulated AC voltages, e.g. for improving the effective potential focused towards the central line (5).

The performance of the invention was tested in an experiment on the basis of a first prototype in the following manner: In a mass spectrometer of the prior art (IONICON® PTR-TOF 8000), the proton transfer reaction chamber supplied by the manufacturer was changed over to a reaction chamber according to the invention, and comparative measurements were made with identical sample gas mixtures in both variants. In each case $H_3O^+$ ions were used as primary ions, and the process parameters gas pressure, electric field strength and temperature were optimized for each of the two variants in relatively long series of tests.

The reaction chamber supplied by the manufacturer is a standard drift tube with ring electrodes to which DC voltages are applied. The axial length of the cylindrical reaction volume of this standard drift tube is 10 cm.

The prototype of the reaction chamber according to the invention is a 3-phase tripole. The length of the likewise cylindrical reaction volume is 7 cm. According to the invention, phase-shifted RF sine voltages having a frequency of 10 MHz and an amplitude of 200 V were applied to the three electrodes.

Table 1 shows the experimental results. Four different analyte gases in the carrier gas air having a relative humidity of approx. 60% at 20° C. were measured. With the reaction chamber according to the invention, a significant increase in the sensitivity of the spectrometer was achieved, which is due to the improved product ion yield and the optimum reduction in the $H_3O^+ \cdot H_2O$ cluster formation. Columns 2 and 3 show the sensitivities with standard drift tube and 3-phase tripole according to the invention in counts per second per parts per billion by volume [cps/ppbv]. Column 4 shows the factor by which the sensitivity could be increased by the prototype. Column 5 shows this factor being extrapolated assuming that the reaction volume according to the invention has the same axial length as the standard drift tube. (In reality, however, the axial length of the reaction volume that was decisive for the reaction time of the ions and thus also for the product ion yield and/or the sensitivity was 10 cm in the standard drift tube and only 7 cm in the prototypes.)

TABLE 1

| analyte | standard drift tube [cps/ppbv] | 3-phase tripole [cps/ppbv] | factor, experimental | factor, extrapolated to same length |
|---|---|---|---|---|
| benzene | 80 | 925 | 11.6 | 16.6 |
| toluene | 101 | 1454 | 14.4 | 20.6 |
| p-xylene | 109 | 1988 | 18.2 | 26 |
| acetone | 111 | 1375 | 12.4 | 17.7 |

The invention claimed is:

1. A method for chemical ionization of a gas mixture by ion-atom reactions or ion-molecule reactions, wherein the gas mixture comprises at least one main component or a carrier gas and one or more reactant gases or analytes, wherein ionization is carried out by reactions with primary ions additionally introduced into the gas mixture, such that product ions are generated from neutral atoms or molecules of the reactant gases, the method comprising:

(a) introducing the gas mixture into a reaction volume having a central line parallel to an axial direction and orthogonal to a radial direction and a radial plane, wherein the reaction volume comprises a first top surface, a second top surface and a lateral surface extending between the two top surfaces and wherein the central line extends from the first top surface to the second top surface and completely within the reaction volume;

(b) introducing primary ions suitable for the chemical ionization of the one or more reactant gas components into the reaction volume;

(c) accelerating the primary ions and generated product ions in the reaction volume by means of a temporally periodic electric field E(x,t), (d) wherein E(x,t) has a radial field vector component $E_r(Z,t)$ which, at all points {Z} lying on the central line, is orthogonal to the central line and which rotates periodically making exactly a 360° rotation in the radial plane during the cycle duration T, and the absolute value $|E_r(Z,t)|$ of which is unequal to zero in more than 80% of the times lying within a cycle duration T, (e) wherein E(x,t) has an axial field vector component $E_{axi}(Z,t)$ which, at all points {Z} lying on the central line, is parallel with respect to the central line and the absolute value $|E_{axi}(Z,t)|$ of which is smaller than the absolute value of the rotating radial component $|E_r(Z,t)|$, and (f) wherein t is time, x is a position vector, Z is a position vector of a point lying on the central line, {Z} is a set of all position vectors Z belonging to the central line, and T is the cycle duration of a 360° rotation of $E_r(Z,t)$.

2. The method according to claim 1, wherein the absolute value $|E_r(Z,t)|$ varies at all points {Z} on the central line by at most 50% of its maximum value $E_{max}(Z)$ in more than 80% of the times lying within a cycle duration T.

3. The method according to claim 1, wherein the absolute value $|E_r(Z,t)|$ varies over at least 80% of the length of the central line by at most 50% of its maximum value.

4. The method according to claim 1, wherein rotation of the radial field vector component $E_r(Z,t)$ corresponds to a harmonic circular motion so that, when shown in Cartesian coordinates (X,Y) being at the respective point Z orthogonal to the central line, $E_r(Z,t)$ meets the following equation:

$$E_r(Z,t) = u_x \cdot [A_x(Z,t) \cdot \sin(\omega t + \Phi_0)] + u_y \cdot [A_y(Z,t) \cdot \cos(\omega t + \Phi_0)],$$

wherein $u_x$ is the unit vector of the X-coordinate and $u_y$ is the unit vector of the Y-coordinate, ω is the angular frequency of rotation, $\Phi_0$ is a global phase offset, and wherein the absolute value $|E_r(Z,t)|$ varies by at most ±10%.

5. The method according to claim 1, wherein the absolute value $|E_r(Z,t)|$ of the rotating field vector $E_r(Z,t)$ is unequal to zero and deviates by at most ±10% from its average value $E_0$ being averaged in terms of time and location at all times t and at all points {Z} lying on the central line, and wherein the axial field component $E_{axi}(Z,t)$ is equal to zero at all times.

6. An apparatus for chemical ionization of a gas mixture by ion-atom reactions or ion-molecule reactions, wherein the gas mixture comprises at least one main component or a carrier gas and one or more reactant gases or analytes, wherein ionization is carried out by reactions with primary ions additionally introduced into the gas mixture, such that product ions are generated from neutral atoms or molecules of the reactant gases, the apparatus comprising:
  (a) a reaction volume having a central line parallel to an axial direction and orthogonal to a radial direction and a radial plane, wherein the volume comprises a first top surface, a second top surface and a lateral surface extending between the two top surfaces and wherein the central line extends from the first top surface to the second top surface and completely within the reaction volume;
  (b) N electrodes, wherein N is an integer larger than or equal to three, wherein each of the N≥3 electrodes is arranged such that it extends from the boundary of the first top surface to the boundary of the second top surface and snuggles from the outside to the reaction volume so that it contacts the lateral surface along its overall extension being tangent to it from the outside,
  (c) an AC voltage source which can be electrically connected to each of the N≥3 electrodes, wherein the AC voltage source is configured such that a periodic AC voltage $U_i(t)$ can be applied to each of the N≥3 electrodes, wherein
  $U_i(t)$ is the AC voltage at the i-th electrode, wherein
  the AC voltages $U_i(t)$ to $U_N(t)$ each have the same cycle duration T or the same frequency f=1/T, wherein
  all AC voltages $U_i(t)$ have a different phase position $\varphi_i$ between 0° and 360° so that each voltage $U_{i>1}(t)$ is temporally shifted with respect to the first voltage $U_1(t)$ by the fraction $\Delta t_i = (\varphi_i/360°) \cdot T$ of the cycle duration T, and wherein,
  when the electrodes are numbered consecutively along the boundary of a top surface in a sense of rotation, the phase positions $\varphi_i$ and $\Delta t_i$ are arranged in ascending order, i.e.

$\varphi_1 = 0° < \varphi_2 < \ldots < \varphi_i < \ldots < \varphi_N < 360°$, and $\Delta t_1 = 0 < \Delta t_2 < \ldots < \Delta t_i < \ldots < \Delta t_N < T.$ 7. The apparatus according to claim 6, characterized in that the N≥3 electrodes are arranged such that in each radial plane an in-circle can be inscribed into them and the arrangement of the N electrodes divides this in-circle in equally-sized segments of a circle having an opening angle of 360°/N, wherein
  the electrodes are configured and arranged such that each section through the electrode configuration being orthogonal to the central line is rotationally invariant with respect to a rotation by 360°/N.

8. The apparatus according to claim 6, wherein the phase positions $\varphi_i$ and $\Delta t_i$ of the N AC voltages $U_i(t)$ meet the following equations $\varphi_i = [(i-1)/N] \cdot 360°$ and $\Delta t_i = [(i-1)/N] \cdot T,$ wherein the same phase difference $\varphi_{i,i+1} = [\varphi_{i-1} - \varphi_i] = 360°/N$ and $\Delta t_{i,i+1} = [\Delta t_{i+1} - \Delta t_i] = T/N$ is present between all two neighboring electrodes.

9. The apparatus according to claim 6, wherein the AC voltages $U_i(t)$ are substantially sinusoidal and at any time t deviate by at most ±20% from the sine function $U_i(t) = U_0 * \sin(\omega t + \varphi_i)$.

10. The apparatus according to claim 6, wherein the central line is bent, or is closed, wherein, in case of a closed central line, the first top surface and the second top surface coincide in one surface.

11. The apparatus according to claim 6, wherein a cross-section through the lateral surface which is orthogonal to the central line changes in the course of the lateral surface from the first top surface to the second top surface.

12. The apparatus according to claim 6, wherein the electrodes and the AC voltage source are configured such that a static electric field can be applied within the reaction volume.

13. The apparatus according to claim 6, wherein the apparatus comprises, in addition to the electrodes, also further electrodes to which DC and/or AC voltages can be applied.

14. The apparatus according to claim 6, wherein the frequency f of the AC voltages $U_i(t)$ ranges between 100 kHz and 100 MHz, the amplitudes $U_0$ of the AC voltages $U_i(t)$ range between 50 V and 10 kV, the gas pressure p of the gas mixture in the reaction volume ranges between 10 mbar and 1 bar, the length L of the reaction volume measured along the central line ranges between 5 mm and 100 mm, and the inner diameter D of the reaction volume ranges between 1 mm and 20 mm.

* * * * *